United States Patent
Cohen et al.

(10) Patent No.: US 6,406,439 B1
(45) Date of Patent: Jun. 18, 2002

(54) PHASE LOCK EVOKED RESPONSE AUDIOMETER

(75) Inventors: Lawrence Thomas Cohen; John Charles Parker; Field Winston Rickards, all of Victoria (AU)

(73) Assignee: The University of Melbourne, Parkville (AU)

( * ) Notice: Subject to any disclaimer, the term of this patent is extended or adjusted under 35 U.S.C. 154(b) by 0 days.

(21) Appl. No.: 09/673,233

(22) PCT Filed: Apr. 22, 1999

(86) PCT No.: PCT/AU99/00303

§ 371 (c)(1),
(2), (4) Date: Dec. 1, 2000

(87) PCT Pub. No.: WO99/53839

PCT Pub. Date: Oct. 28, 1999

(51) Int. Cl.[7] .................................................. A61B 5/00
(52) U.S. Cl. ......................................... 600/559; 381/15
(58) Field of Search ........................ 600/559; 381/1–28, 381/94.1–94.9, 104, 105, 106, 107, 108, 109

(56) References Cited

U.S. PATENT DOCUMENTS

| | | |
|---|---|---|
| 4,462,411 A | 7/1984 | Rickards |
| 5,023,783 A | 6/1991 | Cohen et al. |
| 5,697,379 A | 12/1997 | Neely et al. |
| 5,916,174 A * | 6/1999 | Dolphin ...................... 600/559 |

* cited by examiner

Primary Examiner—Kevin Shaver
Assistant Examiner—Pamela Wingood
(74) Attorney, Agent, or Firm—Dennison, Scheiner & Schultz

(57) ABSTRACT

An evoked response audiometer method and apparatus in which a patient receives an auditory stimulus signal comprising a carrier frequency which is periodically amplitude modulated and frequency modulated whereby the stimulus is at least substantially frequency specific, the brain potential signals of the patient evoked by the auditory signal being sampled to determine whether phase locking to the modulated auditory signal has occurred, the auditory signal being selectively controlled to advance or delay one modulation with respect to the other modulation to cause enhancement of the evoked response to the auditory stimulus.

14 Claims, 9 Drawing Sheets

PHASE LOCK EVOKED RESPONSE AUDIOMETER

FIELD OF THE INVENTION

This invention relates to an improved evoked response audiometer for use in the diagnosis of deafness.

BACKGROUND OF THE INVENTION

The diagnosis of deafness at an early stage in paediatrics is important to enable the early fitting of hearing aids and/or cochlear implants in order to assist language development in a hearing-impaired child. It is also important to be able to diagnose deafness in adults who are unable, due to mental illness or disability, or unwilling, for various reasons, to participate in conventional behavioural deafness testing.

In our U.S. Pat. Nos 4,462,411 (Rickards) and 5,023,783 (Cohen and Rickards), we have described evoked response audiometers which use a continuous auditory tone that is frequency or amplitude modulated, the auditory tone being presented for a sufficiently extended period of time to enable phase-locked steady-state potentials to be evoked in the brain of the person being tested. An electro-encephalograph (EEG) signal from the scalp of the person is manipulated such that the components due to the modulation carried by the auditory stimulus is extracted and detected.

The modulated auditory stimulus produces separate and distinct evoked potentials in the brain depending on the nature of the modulation. These evoked potentials can be difficult to detect, particularly for low sound levels which are less audible to the person being tested.

SUMMARY OF THE INVENTION AND OBJECT

It is therefore an object of the present invention to provide an improved evoked response audiometer incorporating an improved modulation technique which produces stronger evoked potentials using low sound level auditory stimulus signals.

The invention provides an evoked response audiometer comprising means for supplying to a patient an auditory stimulus signal consisting of a carrier frequency which is modulated by at least two different forms of modulation such that the stimulus is at least substantially frequency specific, said auditory signal being presented for a sufficiently extended period of time to enable phase-locked steady-state potentials to be evoked in the brain of the patient, means for sampling the brain potential signals evoked by said auditory signal, and means for analysing said brain potentials to determine whether phase-locking of said brain potentials to the modulated auditory signal has occurred, said means for supplying said auditory signal being selectively controlled to advance or delay one modulation with respect to the other modulation to cause enhancement of the evoked response to the auditory stimulus.

Research has indicated that the combined modulation of the auditory stimulus enables significant improvements in the detection of the evoked potentials whereby evoked potentials of amplitude large enough for detection will be produced by auditory stimuli of lower sound level, and hence lower subjective loudness.

The invention also provides a method of testing for hearing impairment, comprising the steps of supplying to the patient an auditory stimulus signal consisting of a carrier frequency which is modulated by at least two different forms of modulation so that the stimulus is at least substantially frequency specific, presenting the auditory signal for a sufficiently extended period of time to enable phase-locked steady-state potentials to be evoked in the brain of the patient, sampling the brain potential signals evoked by said auditory signal, analysing said brain potentials to determine whether phase-locking of said brain potentials to the modulated auditory signal has occurred, and selectively controlling said auditory signal to advance or delay one modulation with respect to the other modulation to cause enhancement of the evoked response to the auditory stimulus.

In a preferred form of the invention, the auditory stimulus signal is amplitude modulated and frequency modulated, preferably in a periodic manner, such as sinusoidal. The potentials evoked in the brain by amplitude modulation and frequency modulation have been found to differ in phase, indicating different delays in the processing by the auditory system to amplitude modulation and frequency modulation. By compensating for the delay in perception of the amplitude and frequency modulation, the auditory signal compensates for the auditory system process by artificially advancing or retarding in time the amplitude modulation or the frequency modulation relative to each other, resulting in the equalisation of the phase delays occurring in the evoked brain potentials.

Without the necessary equalisation, the response to the amplitude modulated signal and the response to the frequency modulated signal can have a phase relationship which results in response cancellation when the responses are vectorially summed. By compensating for the delays in the actual auditory stimulus, the phase of the two responses can be altered so that the vectorial sum is significantly enhanced beyond the stimulus achieved by the use of amplitude modulation or frequency modulation alone. This enhancement results in a higher detection sensitivity to the stimulus by virtue of an improved signal to noise ratio, and consequently, the hearing threshold determined when using the evoked response audiometer much closer to the true behavioural hearing threshold of the patient under test. As a result, estimations of the true behavioural thresholds from the patients evoked response thresholds are improved.

Depending on the frequency of the carrier, the modulation frequency and the corresponding modulation indexes of the auditory signal, the measured physiological delays will vary. All such delays can be compensated for by adjusting the phase relationship between the AM modulation and the FM modulation of the stimulus signal.

In terms of hearing perception, AM is produced by modulating a pure tone (or sinusoid) whose amplitude is varied in a sinusoidal manner by another sine wave at the modulation frequency. FM is produced by modulating a pure tone whose frequency is varied in a sinusoidal manner by a sine wave at the modulation frequency. When both forms of modulation are combined, the frequency and amplitude can be varied together in a number of subtly different ways. For example, the frequency can be high when the amplitude is high; the frequency can be low when the amplitude is high; the frequency can be midway when the amplitude is high, or the frequency can be midway when the amplitude is low.

The relative phase between the AM signal and the FM signal can be given any value between +/− about 60°, depending on the signal parameters, to produce enhanced evoked potentials in the brain of the patient.

The responses to AM and FM stimuli, detected in the overall EEG activity, differ. To improve the detection process both modulation methods are used together and the phase difference between the AM and FM modulations is selected to result in constructive addition of the AM and FM response components. In a preferred form, this occurs when the phase difference between the AM and FM modulations is about 30°. If the modulation components are about 210° apart, cancellation will occur. The AM/FM stimulus in this case would produce no or very little detected response to the stimulus.

The phase relationship between the AM and FM detection processes depends on the mechanics of the ear and brain physiology. It also depends on the modulation indices used. The modulation indices determine how much the carrier amplitude is changed by amplitude modulation and how much the frequency of the carrier is changed by the frequency modulation.

It is expected that different relative phase delays will be required depending on the patient tested, the carrier and modulation frequencies, and the AM and FM modulation indices used. Norms for different age groups and conscious states are determined experimentally. To this extent the solution of the more appropriate phase difference is initially determined empirically. However, once an appropriate phase difference is determined, it can be used for similar patient types and similar signal parameters. The system may be designed to determine and be used for diagnosis of particular hearing problems when the phase delays used for normal patients do not provide a response as expected by those norms. Calculations indicate a difference in the optimum AM/FM phase relationship of about 30°+/−20° would contain any detection loss to less than about 0.1 dB. If the vectors are more substantially out of phase, a loss of up to about 9.5 dB can occur. For different signal parameters, a difference in phase of up to about +/−60° may produce similar benefits depending on the relative amplitude of the AM and FM responses. If the relative amplitudes are equal, a gain of up to 6 dB will result (see FIG. 10) but if the relative amplitudes are half each other then a loss of benefit results (see FIG. 11).

Calculations indicate that the combined modulations can result in a typical improvement in the signal to noise ratio of about 3.5 dB compared to the response over that of AM used alone. Since the responses being detected are very small compared to the background noise level, this improvement should be considered to be substantial. This assumes the EEG voltage of an FM response is typically half the EEG voltage of an AM response for the same stimulus level.

DESCRIPTION OF PREFERRED EMBODIMENT

Figure 1:
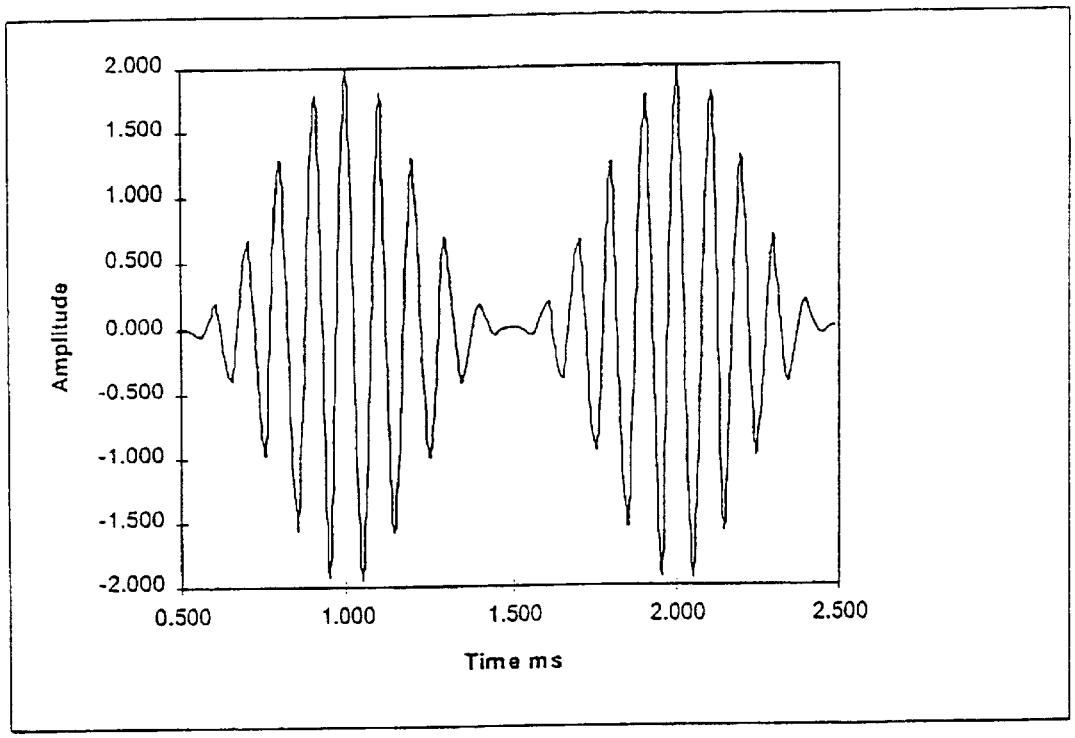
FIG. 1 is a graph of a signal which has been amplitude modulated (AM)
Figure 2:
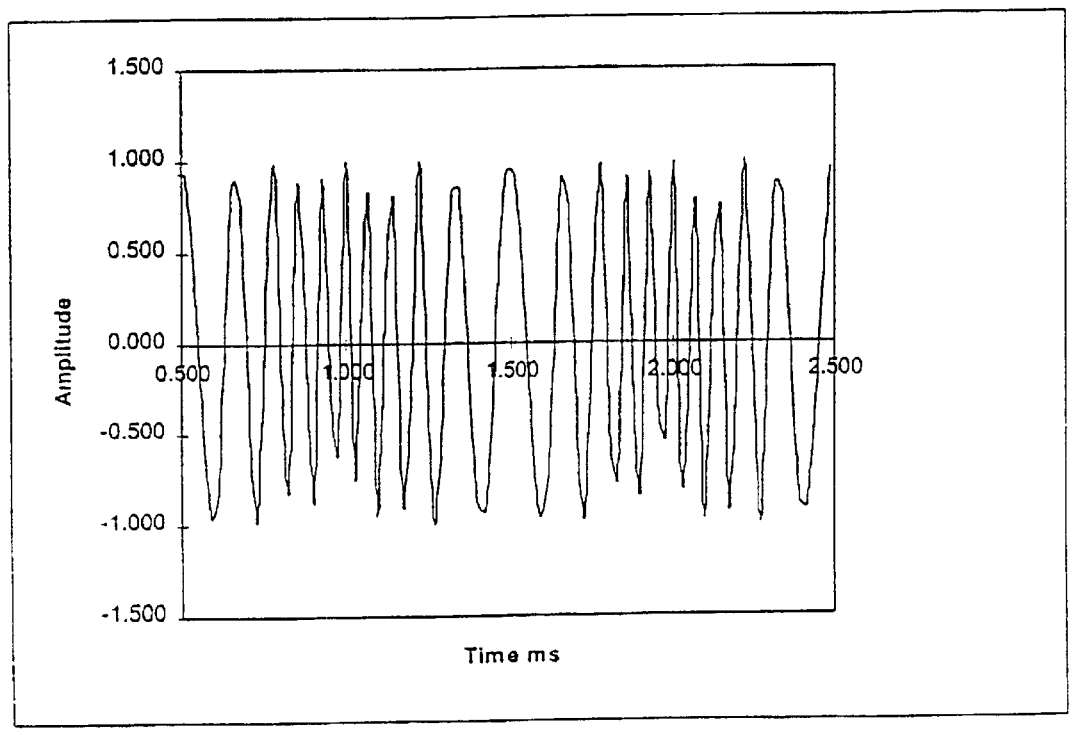
FIG. 2 is a graph of a signal which has been frequency modulated (FM)

The evoked response audiometer embodying the invention uses digital signal processing (DSP) techniques for the generation of an auditory signal or stimulus and the detection of the response to the stimulus in the EEG activity representing the evoked potentials produced by the auditory signal. Consequently the processes used are implemented in software contained within the digital signal processor circuit used. This software is under direction of another software program which resides on a personal computer (PC) using Windows95™ or a similar computer and/or operating system.

Conventional signal processing algorithms used in the DSP software, when used in conjunction with each other, produce the required results. Frequency modulation and phase modulation are considered synonymous, as the modulation used is a single sinusoidal tone. Electronic hardware of the type described in our earlier U.S. Pat. Nos. 4,462,411 and 5,023,783, the contents of which are incorporated into the present specification by cross reference, is incorporated into the DSP and PC software programs. Delta-Sigma analog to digital and digital to analog converters are used to translate back and forth between the analog domain and the digital domain. The EEG signal is amplified by means of a battery operated electronic circuit and is then transmitted using a fibre optic cable to the main processing circuitry. This enhances the safety of the patient under test.

As the embodiment is implemented by programming mathematical algorithms into assembly code for the DSP to execute, these algorithms express the function of the apparatus. The algorithms which describe the AM/FM relative angle specifically are therefore presented in mathematical form. The AM/FM relative angle is given the symbolic label of $\phi$.

The computer program, under the direction of the operator, can control:

$A_c$ amplitude of unmodulated carrier $m_a$ AM modulation index (0→1.0)

$f_m$ modulation frequency $f_c$ carrier frequency $\beta$ the peak phase deviation or FM modulation index in radians $f_d$ the frequency deviation $\phi$ the AM/FM relative modulation phase The following preferred equations are implemented in the DSP software using the values specified by the user listed above.

1) For signal tone AM modulation AM $$e_{AM}(t) = A_c[m_a \cos(2\pi f_m t) + 1] \cos(2\pi f_c t) \qquad 1)$$

Where:

$e_{AM}(t)$ voltage at time t $A_c$ amplitude of unmodulated carrier $m_a$ AM modulation index (0→1.0)

$f_m$ modulation frequency $f_c$ carrier frequency

The increase in the signal power level in dB for a specified AM modulation index over that of a pure sine wave output (ie unmodulated carrier or pure tone where the AM modulation index=0) can be calculated as follows:

$$\Delta P_{dB} = 10 \log_{10}\left(1 + \frac{m_a^2}{2}\right) = 1.7609\, dB \text{ for } 100\% \text{ modulation} \quad 2)$$

This equation still holds when FM modulation and AM modulation are used together.

2) For signal tone FM modulation FM $$e_{FM}(t) = A_c \cos\left[2\pi f_c t + \left(\frac{f_d}{f_m}\right)\sin(2\pi f_m t)\right] \quad 3)$$

Since the frequency deviation is constant, the modulation index $\beta 2 = f_d/f_m$ varies with the modulating frequency. 4)

Where:

$e_{FM}(t)$ voltage at time t
$A_c$ amplitude of unmodulated carrier
$\beta$ the peak phase deviation or modulation index in radians
$f_d$ the frequency deviation
$f_m$ modulation frequency
$f_c$ carrier frequency The modulation index has no effect on the output power level which remains constant.

Also $$e_{FM}(t) = A_c \cos\left[2\pi f_c t + \left(\frac{m_{fm}}{2\pi f_m}\right)\sin(2\pi f_m t)\right] \quad 5)$$

$$e_{FM}(t) = A_c \cos\left[2\pi f_c t + \left(\frac{f_{dev}}{f_m}\right)\sin(2\pi f_m t)\right] \quad 6)$$

Where $m_{fm}=\Delta\omega_c=2\pi f_{dev}$ is the peak frequency deviation 7)

$\beta = \Delta\theta =$ 8)

$\left(\frac{\Delta\omega_c}{2\pi f_m}\right) = \left(\frac{m_{fm}}{2\pi f_m}\right) = \left(\frac{f_{dev}}{f_m}\right)$ is the peak phase deviation in radian 3) For signal tone AM/FM modulation, AM/FM, and a AM/FM relative phase angle of φ.

$$e_{AM/FM}(t) = A_c[m_a\cos(2\pi f_m t) + 1]\cos\left[2\pi f_c t + \left(\frac{f_{dev}}{f_m}\right)\sin(2\pi f_m t + \phi)\right] \quad 9)$$

or alternatively $$e_{AM/FM}(t) = A_c[m_a\cos(2\pi f_m t + \phi) + 1]\cos\left[2\pi f_c t + \left(\frac{f_{dev}}{f_m}\right)\sin(2\pi f_m t)\right] \quad 10)$$

Where:

$e_{AM/FM}(t)$ voltage at time t
φ AM/FM relative modulation phase

4) For signal tone PM modulation PM $$e_{PM}(t) = A_c \cos[2\pi f_c t + m_{pm}\cos(2\pi f_m t)] \quad 11)$$

Where $m_{pm}=\Delta\theta$ the peak phase deviation 12)

5) FM and PM can be considered equal when single tone modulation is used.

$$\omega_{PM}(t) = \omega_c - m_{pm}\omega_m \sin \omega_m t \quad 13)$$

and $$\omega_{FM}(t) = \omega_c + \Delta\omega_c \cos \omega_m t \quad 14)$$

If $\Delta\omega_c = m_{pm}\omega_m$ then $m_{pm} = \frac{\Delta\omega_c}{\omega_m} = \beta = \frac{f_{DEV}}{f_m} = \Delta\theta$ 15)

So if $m_{pm}=\beta$ then the modulation methods are identical except for the phase relationship between the carrier and the modulation ie SIN vs COS.

6) AM/FM Spectrum

The AM and FM equations 1) & 3) are multiplied in time or their Fourier equivalents are convolved to produce the following, keeping in mind that the AM & FM frequency is identical but the AM and FM phase is separated by φ ie the relative phase between the AM and FM.

Since some software packages, such as Excel™ and Matlab™, do not provide Bessel functions results for negative orders, we compensate by using the following additional equation to indicate the sign of the Bessel function for all orders, negative or positive and supplying the Bessel function itself with the absolute order.

$$f(n) = \begin{bmatrix} n < 0, (-1)^n \\ n >= 0, 1 \end{bmatrix} \quad 16)$$

and $\delta(\omega)$ is a Dirac delta function or unit impulse and using the two Fourier transform pairs $$\delta(\omega-\omega_x) = F\{e^{j\omega_x t}\}$$

and $$\delta(\omega+\omega_x) = F\{e^{-j\omega_x t}\}$$

and where $\omega_x$ is the angular frequency of x
$J_n(x)$ the Bessel functions of the first kind of order n for x
$F\{x\}$ is the Fourier transfrom of x
$s(x)$ is frequency spectrum of x
* convolution symbol $$e_{AM}(t) = A_c\left\{\cos(\omega_c t) + \frac{m_a}{2}[\cos((\omega_c - \omega_m)t) + \cos((\omega_c + \omega_m)t)]\right\} \quad 17)$$

$$e_{FM}(t) = A_c \sum_{n=-\infty}^{\infty} f(n)J_{|n|}(\beta)\cos((\omega_c + n\omega_m)t) \quad 18)$$

Convolving the AM and FM signals to find the spectrum:

$$s(\omega) = F\left\{A_c\cos\left[\omega_c t + \left(\frac{f_{dev}}{f_m}\right)\sin(\omega_m t)\right]\right\} * F\{A_c[m_a\cos(\omega_m t + \phi) + 1]\} \quad 19)$$

-continued and if $FM(\omega) = F\{FM\}$ then $FM(\omega) = A_c \sum_{n=-\infty}^{\infty} f(n) J_{|n|}(\beta)$ (20)

then $s(\omega) =$ (21)

$$FM(\omega) * \left[ A_c \delta(\omega) + \frac{A_c m_a e^{j\phi}}{2} \delta(\omega - \omega_m) + \frac{A_c m_a e^{-j\phi}}{2} \delta(\omega + \omega_m) \right]$$

$$s(\omega) = A_c \left[ FM(\omega) + \frac{m_a e^{j\phi}}{2} FM(\omega - \omega_m) + \frac{m_a e^{-j\phi}}{2} FM(\omega + \omega_m) \right]$$

where $e^{j\phi} = \cos\phi + j\sin\phi$
and therefore in the summation the three terms represent in order as presented:
  spectrum due to the carrier
  spectrum due to the lower AM sideband
  spectrum due to the upper AM sideband $$e_{AM/FM}(t) = A_c \sum_{n=-\infty}^{\infty} \left\{ \begin{pmatrix} f(n) J_{|n|}(\beta) + \\ \frac{m_a}{2} \begin{bmatrix} (f(n+1) J_{|n+1|}(\beta)(\cos\phi + j\sin\phi)) \\ (f(n-1) J_{|n-1|}(\beta)(\cos\phi - j\sin\phi)) \end{bmatrix} \end{pmatrix} \cdot \cos((\omega_c + n\omega_m)t) \right\}$$ (22)

When $\phi$ is set to zero and if the AM modulation index $m_a$ is set to zero then equation 22) equals equation 18) ie FM. When $\phi$ is set to zero and if the FM modulation index $\beta$ is set to zero then equation 22) equals equation 17) ie AM since $J_0(0)=1$ and the remaining orders of n equal 0. If $J_0(0)$ is then replaced with zero the result is double sideband modulation (DSB).

The magnitude can be found by summing the Real and Imaginary terms then taking the square root of the sum of the squares for each Real and Imaginary sum found.

In the illustrated modulations of FIGS. 3 to 6, the following features are present.

Figure 3:
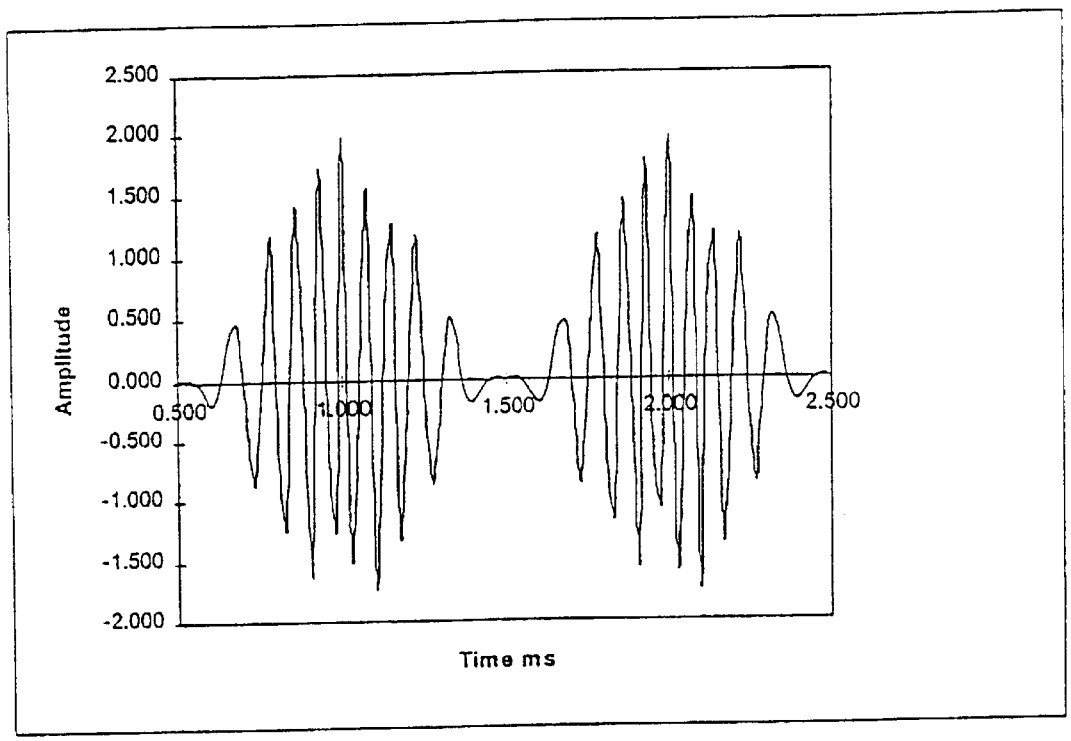
FIGS. 3 to 6 are graphs illustrating AM/FM modulation.

In FIG. 3 the carrier frequency is at its highest when the modulation frequency amplitude is at its highest.

Figure 4:
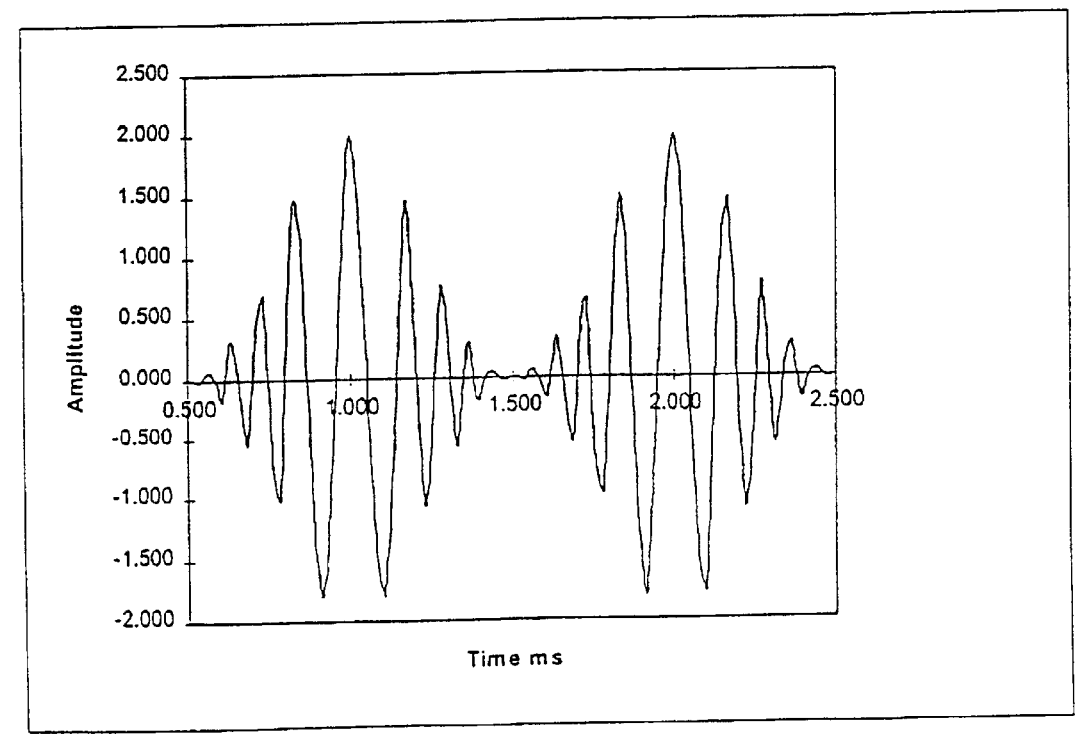

In FIG. 4 the carrier frequency is at its highest when the modulation frequency amplitude is at its lowest.

Figure 5:
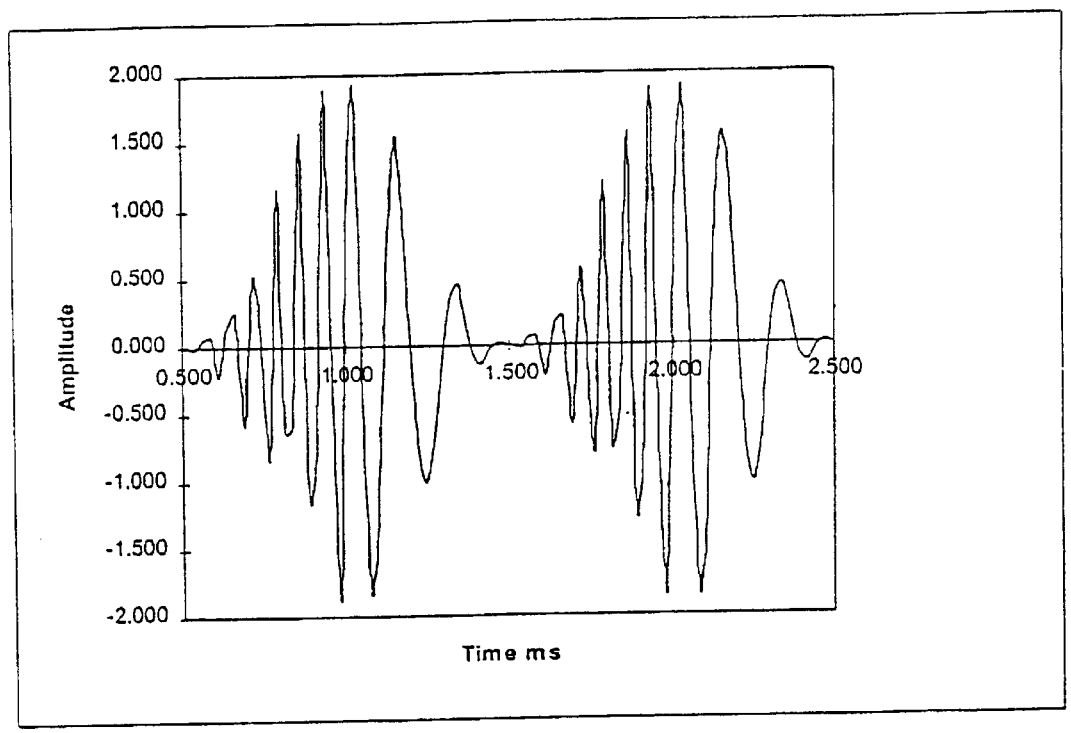

In FIG. 5 the carrier frequency is at its highest when the modulation frequency amplitude has risen to half its maximum amplitude.

Figure 6:
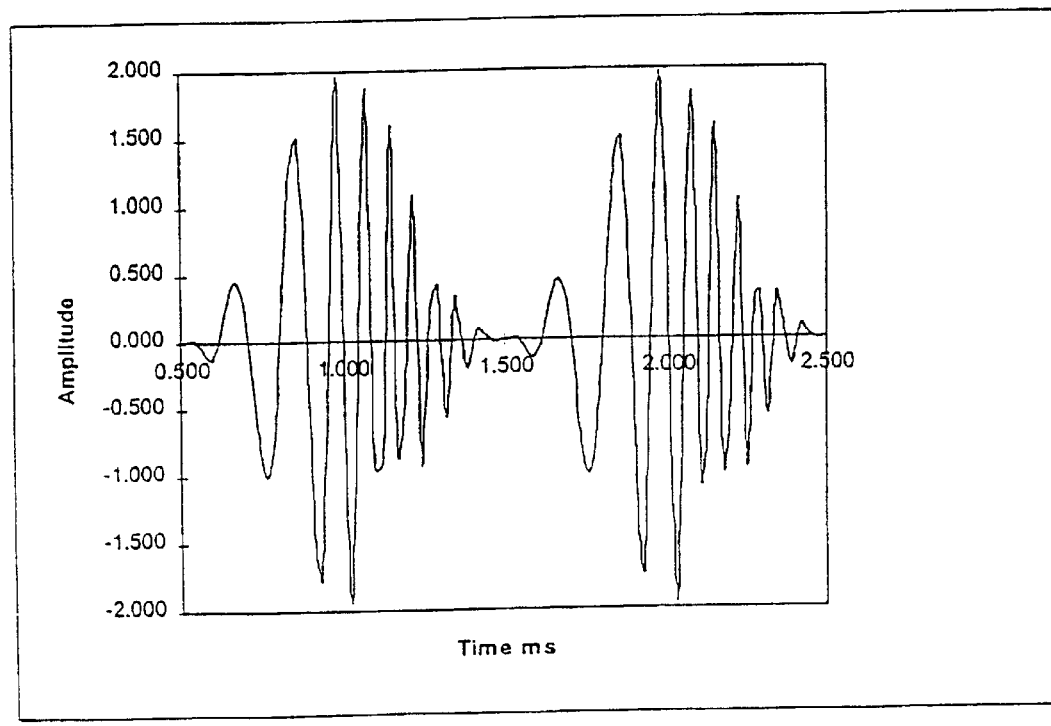
Figure 7:
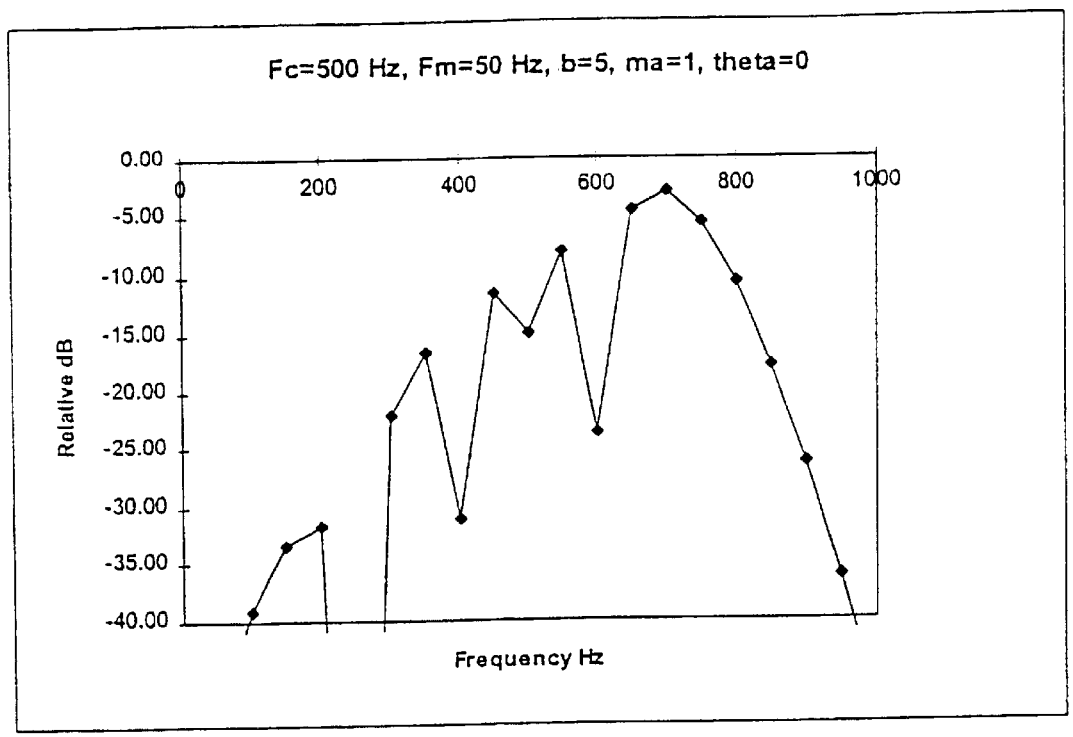
FIGS. 7 and 8 illustrate the envelopes for the spectra of AM/FM modulation for the time waveforms of FIGS. 3 and 4 respectively, with the relative amplitudes in dB shown against frequency.
Figure 8:
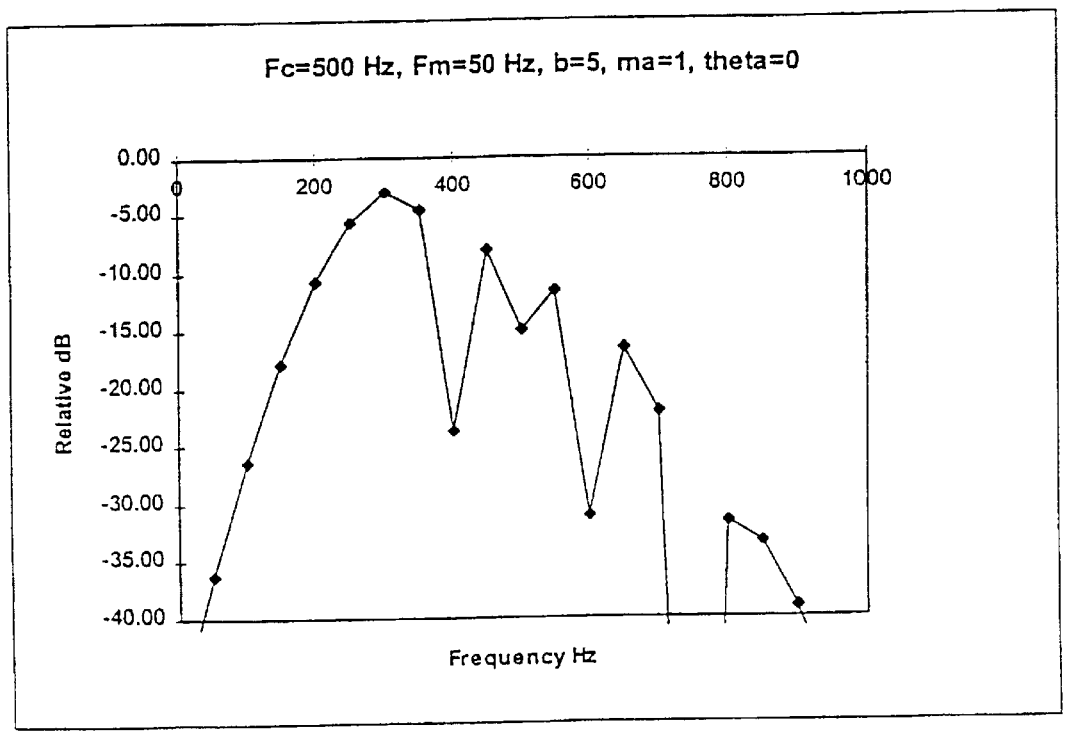
Figure 9:
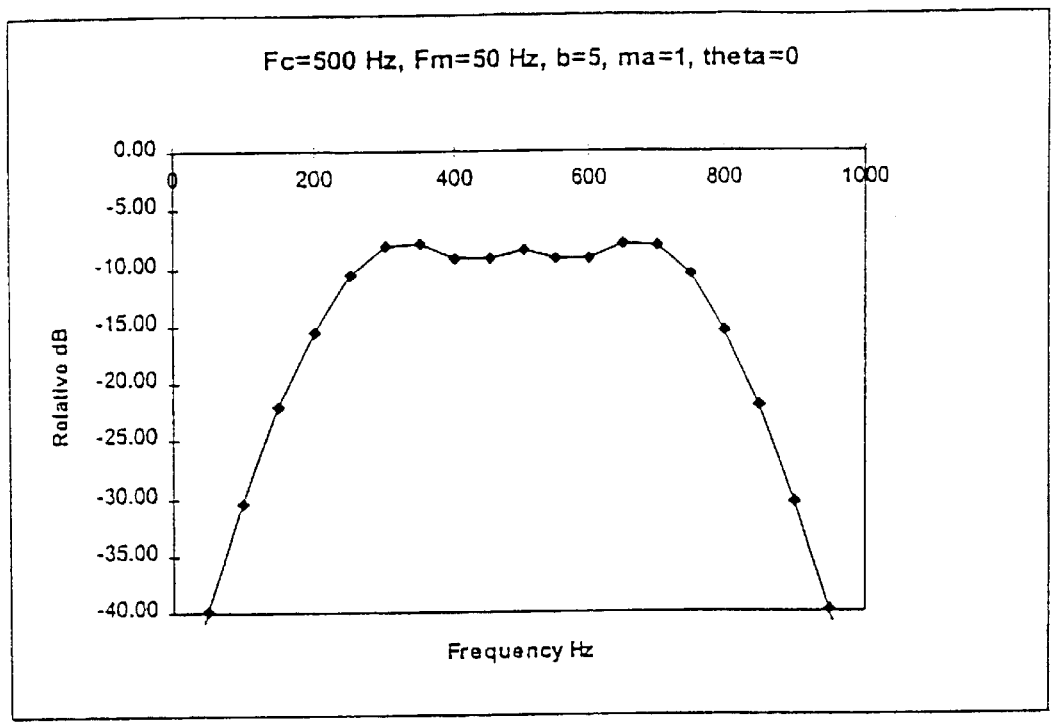
FIG. 9 illustrates the envelopes for the spectra of AM/FM modulation for the time waveforms of FIGS. 5 and 6 respectively, with the relative amplitudes in dB shown against frequency.

In FIG. 6 the carrier frequency is at its highest when the modulation frequency amplitude has fallen to half its maximum amplitude.

Figure 10:
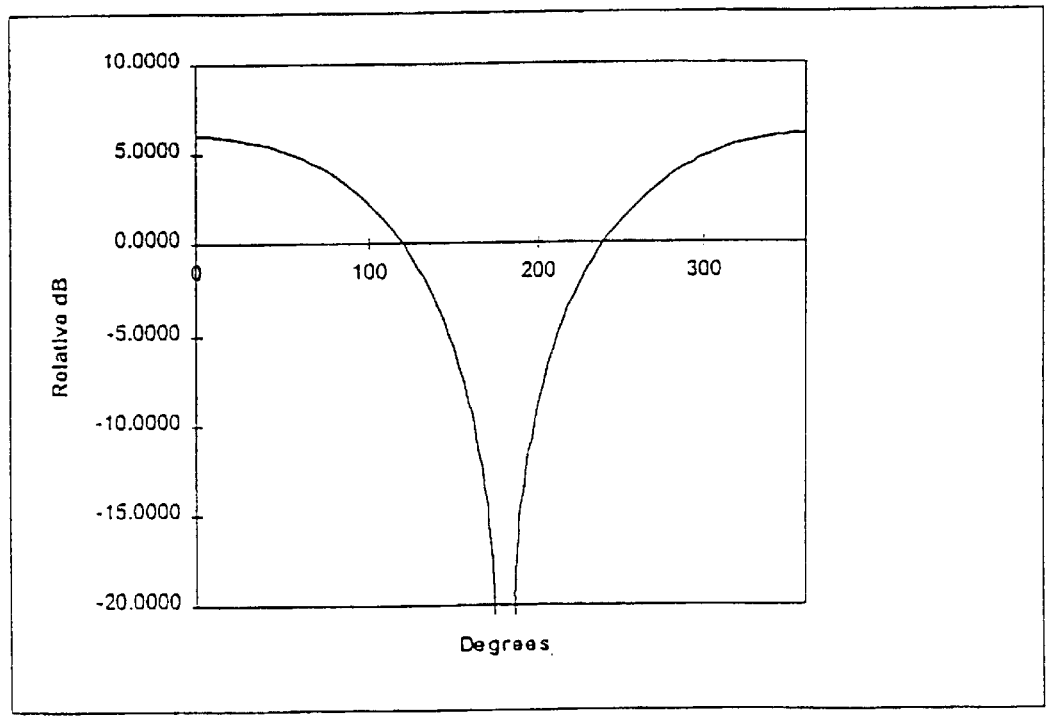
FIGS. 10 and 11 illustrate the gain or loss expected in dB when the AM and FM evoked responses are of the same amplitude and half or double the amplitude respectively compared to an AM response only.
Figure 11:
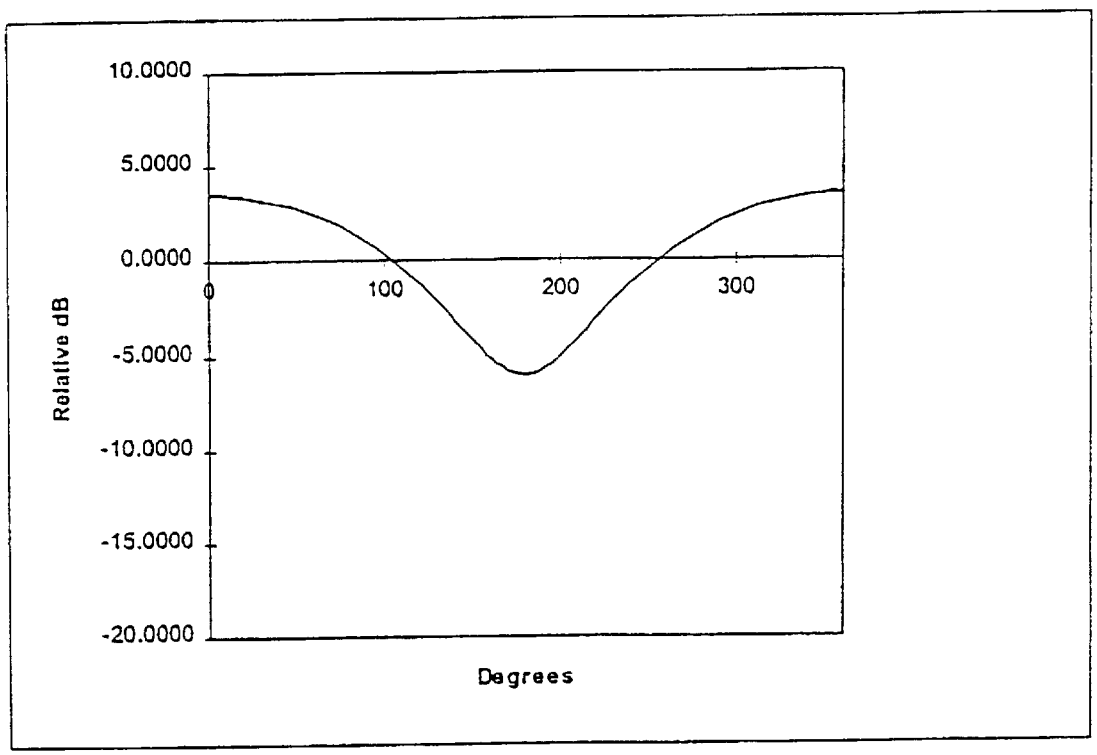

Referring to FIGS. 10 and 11, as the relative phase is changed the two responses either enhance (at 0 degrees) or counteract (at 180 degrees) each other. FIG. 11 is the same as FIG. 10 but the FM response is half the level of the AM response.

Figure 12:
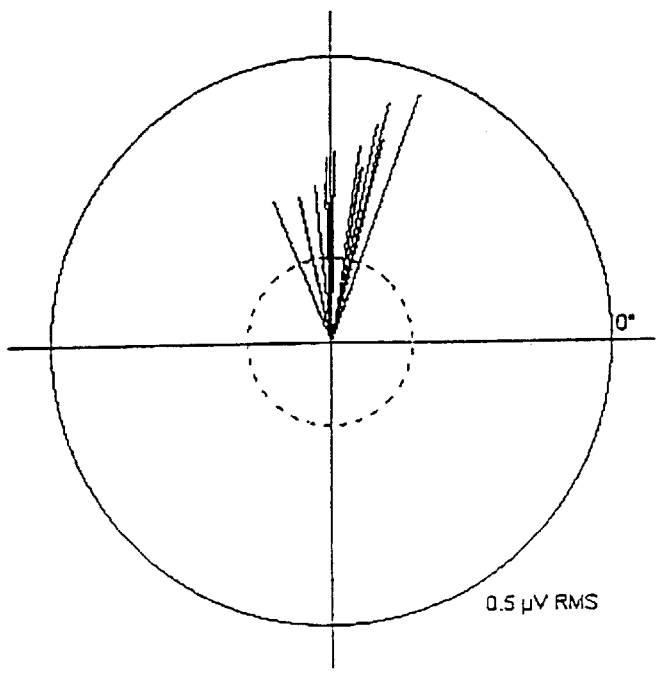
FIGS. 12 to 15 are graphs of vector diagrams showing amplitude vs phase, illustrating responses evoked from a single subject.
Figure 14:
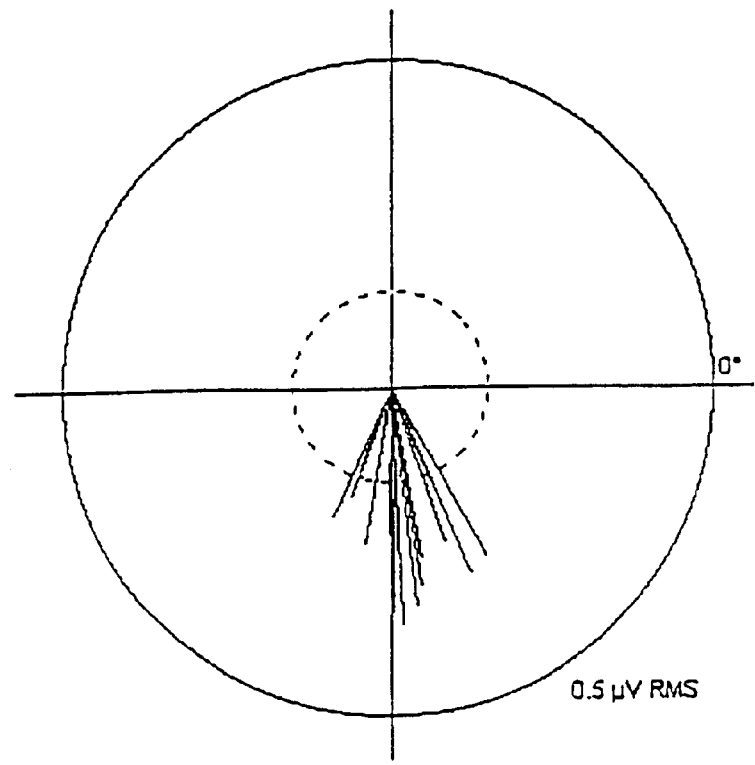

FIGS. 12 and 14 show the individual responses for AM and FM. In these figures the responses are approximately 180 degrees apart.

Figure 13:
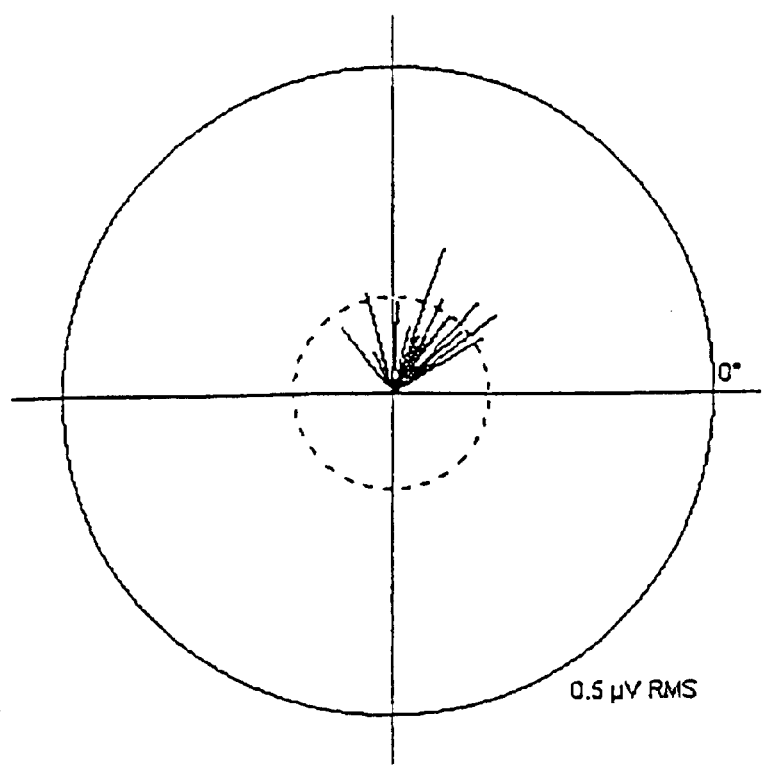

FIG. 13 shows the result when the vectors in FIGS. 12 and 14 are combined. The individual AM and FM responses oppose each other and the AM/FM response is reduced. The reduction is approximately one half, ie a loss of about 4 to 6 dB, as indicated by the length of the vectors.

Figure 15:
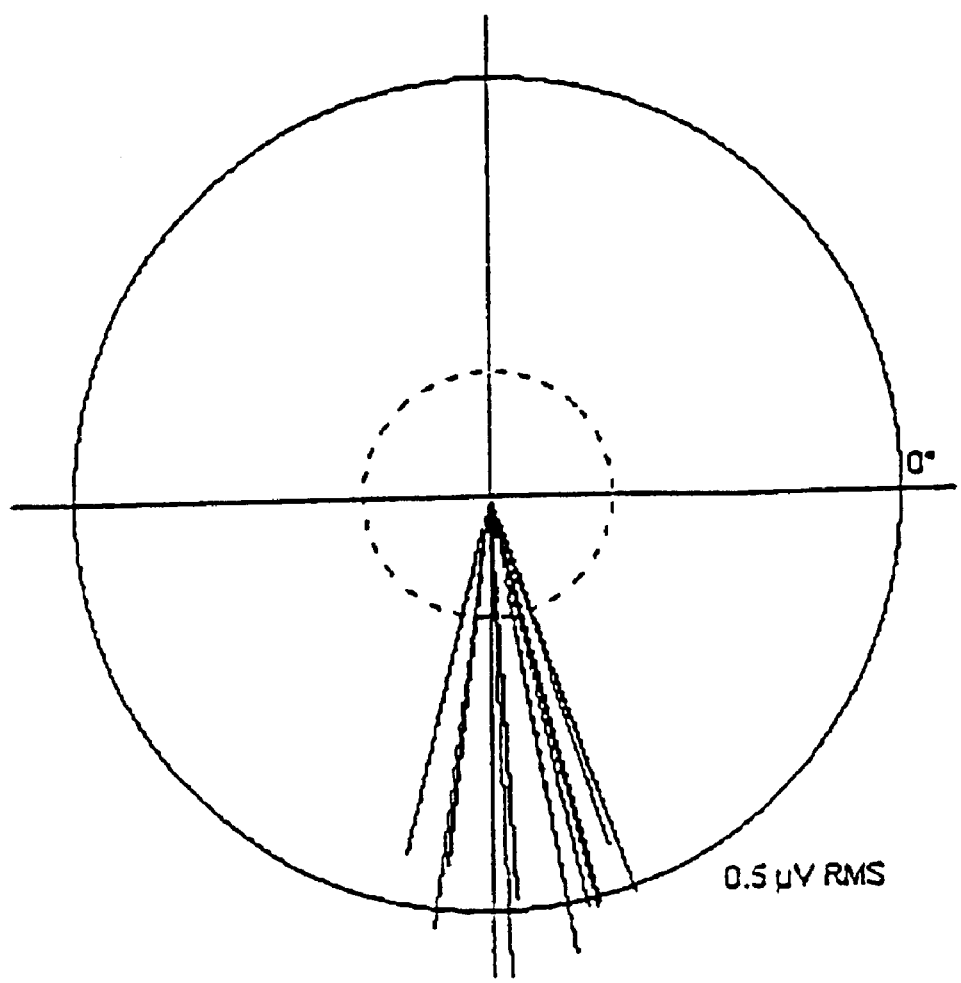

FIG. 15 shows the result when the vectors in FIGS. 12 and 14 are combined. However in this case assume FIG. 12 has been rotated 180 degrees to match the direction of FIG. 14. The rotation is brought about by adjusting the relative AM/FM angle of the stimulus. The individual AM and FM responses now reinforce each other and the AM/FM response is enhanced. The improvement is approximately twice, i.e. a gain of about 4 to 6 dB, as indicated by the length of the vectors.

FIGS. 13 and 15 actually indicate that there is some small phase misalignment in the enhancement or cancellation of the vectors or alternatively the AM and FM responses are not of equal amplitude. Consequently the deep null shown in figure ten is not achieved when the vectors are opposing as the vector diagram FIG. 13 does show a response, albeit small one. FIG. 11 is perhaps more representative of what is being achieved given the four vector diagrams presented.

Figure 16:
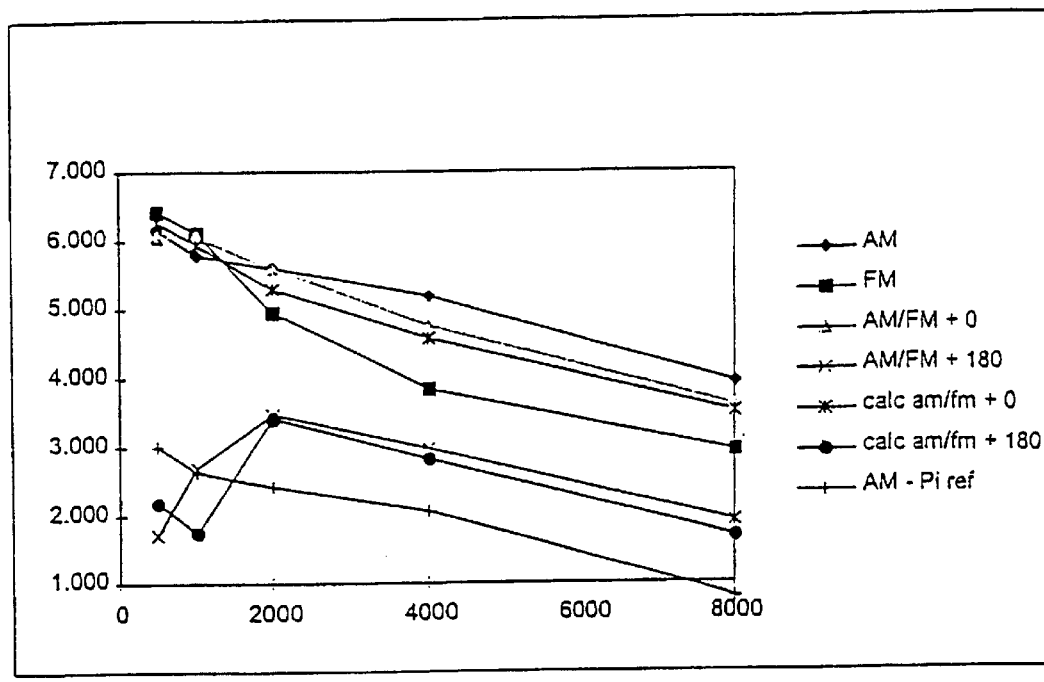
FIG. 16 illustrates graphs of animal tests showing the difference in phase in radians between the auditory stimulus and the evoked response and the frequency of the carrier at a modulation frequency of 140 Hz.

FIG. 16 illustrates data collected from Greyhound dogs, while anaesthetised, and shows the phase recorded from subject four using a stimulus level of 50 dB HL at carrier frequencies of 500, 1k, 2 k and 4 KHz using different modulation types. The results for four types of modulation include:

The phase response using only amplitude modulation at 0°

The phase response using only frequency modulation at 0°

The phase response using AM/FM with a relative phase of 0°

The phase response using AM/FM with a relative phase of 180°

In the results labelled as "calc", the recorded data from the AM and FM only tests were combined vectorially to see if the actual recorded AM/FM tests with relative phases of 0 and 180° could be duplicated by calculation alone. The calculated values match the recorded values well. It was found the AM signal needed to be in the range 1.2 to 1.4 times the FM signal voltage level to match the AM/FM recorded data.

The recorded AM/FM response with a relative phase of 0° is a more precise match with the calculated values than the recorded AM/FM response with a relative phase of 180°. The 180° relative phase responses are less accurate as the cancellation effect diminishes the amplitude of the response compared to the background EEG noise, ie. the signal to noise ratio diminishes. Under these circumstances the measured phase is more prone to error.

The line marked "AM—Pi ref" is the AM result with a relative angle of 0° shifted 180° and is used as a reference line. From 500 Hz to 2000 Hz, the AM and FM signals are very close to being in phase. Therefore the AM/FM result for these carrier frequencies, using a relative phase of 180°, should intersect the reference line, as it does.

Figure 17:
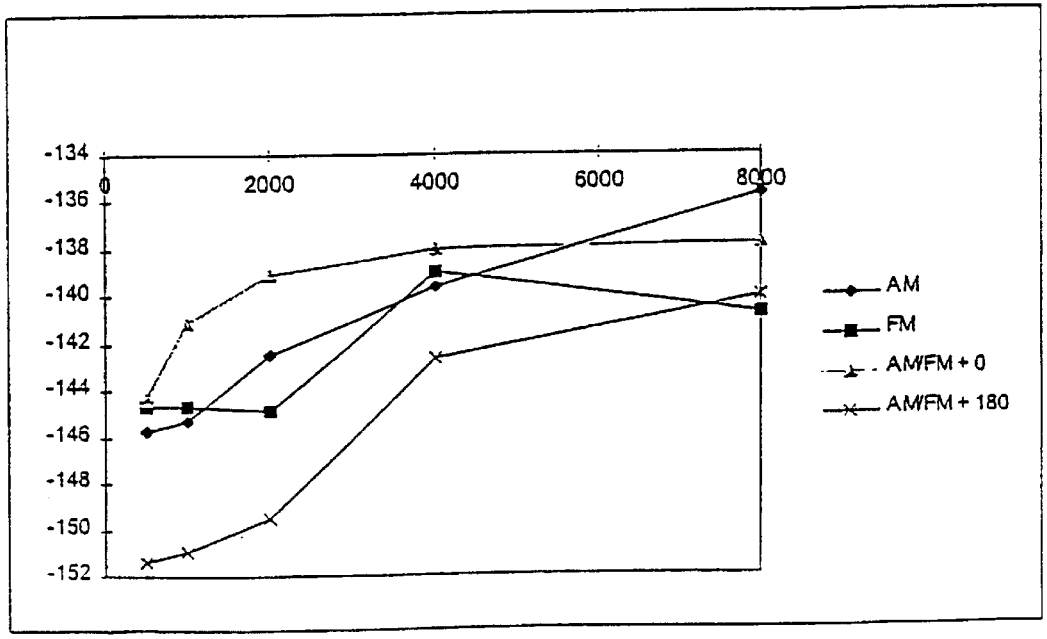
FIG. 17 illustrates graphs of the evoked response voltages and dB relative to one volt against the frequency of the carrier at a modulation frequency of 140 Hz.

FIG. 17 shows the voltage of the EEG signal in dB referenced to one Volt. At carrier frequencies 500 to 2000 Hz where the AM and FM signals are very close to being in phase, we find that the combined signal voltage using AM/FM with a relative phase of 0° is enhanced over that of AM or FM alone. Conversely using AM/FM with a relative phase of 180° the signal level is considerably reduced due to cancellation. It follows from these results that relative phases other than 0° will result in further enhanced evoked potentials at the same or different stimulus signal parameters.

While the preferred modulation modes are AM and FM, other continuous modulation modes may be able to be used with acceptable results.

It will also be appreciated that various modifications and/or alterations may be made to the system described above without departing from the scope and spirit of the invention.

We claim:

1. An evoked response audiometer comprising means for supplying to a patient an auditory stimulus signal consisting of a carrier frequency which is modulated by at least two different forms of modulation such that the stimulus is at least substantially frequency specific, said auditory signal being presented for a sufficiently extended period of time to enable phase-locked steady-state potentials to be evoked in the brain of the patient, means for sampling the brain potential signals evoked by said auditory signal, and means for analysing said brain potentials to determine whether phase-locking of said brain potentials to the modulated auditory signal has occurred, said means for supplying said auditory signal being selectively controlled to advance or delay one modulation with respect to the other modulation to cause enhancement of the evoked response to the auditory stimulus.

2. The audiometer of claim 1, wherein the auditory signal is amplitude modulated and frequency modulated.

3. The audiometer of claim 2, wherein the auditory signal is modulated in a periodic manner.

4. The audiometer of claim 1, wherein the means for supplying said auditory signal is selectively controlled so that there is a difference in phase of up to about +/−60°.

5. The audiometer of claim 4, wherein the difference in phase is about +/−30°+/−20°.

6. A method of testing for hearing impairment, comprising the steps of supplying to the patient an auditory stimulus signal consisting of a carrier frequency which is modulated by at least two different forms of modulation such that the stimulus is at least substantially frequency specific, presenting the auditory signal for a sufficiently extended period of time to enable phase-locked steady-state potentials to be evoked in the brain of the patient, sampling the brain potential signals evoked by said auditory signal, analysing said brain potentials to determine whether phase-locking of said brain potentials to the modulated auditory signal has occurred, and selectively controlling said auditory signal to advance or delay one modulation with respect to the other modulation to cause enhancement of the evoked response to the auditory stimulus.

7. The audiometer of claim 6, wherein the auditory signal is amplitude modulated and frequency modulated.

8. The audiometer of claim 7, wherein the auditory signal is modulated in a periodic manner.

9. The audiometer of claim 6, wherein the means for supplying said auditory signal is selectively controlled so that there is a difference in phase of up to about +/−60°.

10. The audiometer of claim 9, wherein the difference in phase is about +/−30°+/−20°.

11. The audiometer of claim 2, wherein the means for supplying said auditory signal is selectively controlled so that there is a difference in phase of up to about ±60°.

12. The audiometer of claim 3, wherein the means for supplying said auditory signal is selectively controlled so that there is a difference in phase of up to about ±60°.

13. The audiometer of claim 7, wherein the means for supplying said auditory signal is selectively controlled so that there is a difference in phase of up to about ±60°.

14. The audiometer of claim 8, wherein the means for supplying said auditory signal is selectively controlled so that there is a difference in phase of up to about ±60°.

* * * * *

UNITED STATES PATENT AND TRADEMARK OFFICE
CERTIFICATE OF CORRECTION

PATENT NO.     : 6,406,439 B1
DATED          : June 18, 2002
INVENTOR(S)    : Lawrence Thomas Cohen et al.

It is certified that error appears in the above-identified patent and that said Letters Patent is hereby corrected as shown below:

<u>Title page,</u>
Item [22], "PCT Pub. Date", insert:
-- [30]     Foreign Application Priority Data
April 22, 1998  (AU) ........................................ PP 3137 --

Signed and Sealed this

Thirteenth Day of May, 2003

JAMES E. ROGAN
*Director of the United States Patent and Trademark Office*